United States Patent
Baynham et al.

(10) Patent No.: US 8,262,666 B2
(45) Date of Patent: Sep. 11, 2012

(54) IMPLANTABLE DISTRACTOR

(75) Inventors: Bret O. Baynham, Jupiter, FL (US); G. Clay Baynham, Jupiter, FL (US); Matthew G. Baynham, Jupiter, FL (US); David R. Campbell, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 1282 days.

(21) Appl. No.: 11/741,257

(22) Filed: Apr. 27, 2007

(65) Prior Publication Data

US 2008/0269758 A1 Oct. 30, 2008

(51) Int. Cl.
*A61B 17/56* (2006.01)

(52) U.S. Cl. .............. 606/99; 623/17.16; 606/86 A; 606/90; 606/914

(58) Field of Classification Search .... 623/17.11–17.16; 606/90, 99, 105
See application file for complete search history.

(56) References Cited

U.S. PATENT DOCUMENTS

| | | | |
|---|---|---|---|
| 5,658,336 A * | 8/1997 | Pisharodi | 623/17.16 |
| 5,893,890 A * | 4/1999 | Pisharodi | 623/17.16 |
| 6,214,050 B1 * | 4/2001 | Huene | 623/17.15 |
| 6,309,421 B1 * | 10/2001 | Pisharodi | 623/17.16 |
| 6,558,424 B2 * | 5/2003 | Thalgott | 623/17.16 |
| 6,746,484 B1 | 6/2004 | Liu et al. | |
| 6,773,460 B2 * | 8/2004 | Jackson | 623/17.15 |
| 7,195,643 B2 * | 3/2007 | Jackson | 623/17.11 |
| 7,214,243 B2 * | 5/2007 | Taylor | 623/17.11 |
| 7,819,921 B2 * | 10/2010 | Grotz | 623/17.11 |
| 7,850,733 B2 * | 12/2010 | Baynham et al. | 623/17.11 |

\* cited by examiner

*Primary Examiner* — Eduardo C Robert
*Assistant Examiner* — Jerry Cumberledge
(74) *Attorney, Agent, or Firm* — McHale & Slavin, P.A.

(57) ABSTRACT

A spinal implant for stabilizing two adjacent vertebrae having a damaged disc therebetween is assembled in situ. An elongated tool is used to insert a flat U-shaped distractor in the disc space through a low profile incision with both legs of the U-shaped distractor contacting both end plates of the adjacent vertebrae. The tool is rotated 90 degrees rotating the distractor 90 degrees so that each leg of the distractor contacts one end plate of the adjacent vertebrae, respectively, to restore intervertebral space. An elliptical bone tray is slid along the tool to seat within the U-shaped distractor. The tool is removed and a retainer replaces it to lock the bone tray and the distractor together. A screw is used to lock the bone tray to the distraction device, the screw slides down the cannula which is the tool inserted over the rod that the distraction implant is attached to.

5 Claims, 5 Drawing Sheets

IMPLANTABLE DISTRACTOR

FIELD OF THE INVENTION

This invention relates to the field of orthopedic surgery and to spinal implants, in particular.

BACKGROUND OF THE INVENTION

The spinal disc is the natural shock absorber located between all vertebrae. In the event it becomes traumatized through injury or degenerates through age or disease, the intervertebral space is reduced through compression and the relative movement of adjacent vertebrae causes pain. The surgical approach to this problem is to relieve the compression, stabilize the adjacent vertebrae and provide for a natural fusing of the vertebrae into one unit.

There are many spinal implants used to stabilize two adjacent vertebrae to prevent relative movement until the vertebrae are fused together by boney ingrowth through and around the implant. Generally these implants are in three groups, i.e., bone plates, pedicle screw/rod constructs and spinal cages. The bone plates span the intervertebral space and are affixed to the two adjacent vertebrae anteriorly by bone screws. Pedicle screw/rod constructs span the vertebral bodies posteriorly and are often connected with cross-links.

The spinal cages are inserted between the adjacent vertebrae and are usually seated into to the end plates of the adjacent vertebrae. To gain access to the intervertebral space, a site is prepared by removing a portion or all of the spinal disc. A wedge shaped distractor is inserted into the site to gradually separate the adjacent vertebrae until the desired intervertebral space is achieved and cut into the end plates of the adjacent vertebrae. Once the site is prepared, the distractor is removed and the spinal implant is inserted into the disc space. The spinal implant may be packed with bone growth material, bone chips, a combination of both, or other material. The implant usually has openings to allow boney ingrowth to occur. One such device is taught by Liu et al, U.S. Pat. No. 6,746,484 B1.

What is needed in the art is a less complex spinal implant methodology using fewer instruments to reduce surgical time and resulting in a more secure union between the implant and the spine.

SUMMARY OF THE PRESENT INVENTION

Disclosed is a spinal implant kit for fusing adjacent vertebrae. The kit includes an elongated tool, a distractor, a bone tray, and a retainer. The distractor is defined as a base having two legs, each leg joined at one end to the base forming a U-shaped outline. The base has a removable attachment removably connected to an end of the elongated tool, each leg having serrations adapted to engage the end plates of adjacent vertebrae, respectively. The bone tray includes an open top side and an open bottom side, the top side and the bottom side adapted to engage the end plates of adjacent vertebrae, respectively, the bone tray having a sidewall connecting the top side and the bottom side, the sidewall having an bore therethrough. The tool is slidably extending through the bore whereby the distractor is adapted to be inserted between adjacent vertebrae using the tool, the tool adapted to rotate the distractor to engage the serrations and the end plates, the bone tray is adapted to slide along the tool to contact the distractor, the tool is adapted to be removed from the removable attachment of the distractor and the bone tray. The retainer is adapted to be inserted into the bore in the bone tray and the retainer is affixed to the removable attachment in the distractor locking the bone tray and the distractor together.

Therefore, it is an objective of this invention to provide a spinal implant to be assembled in situ.

It is another objective of this invention to provide an implantable distractor for site preparation and establishment of proper intervertebral space.

It is a further objective of this invention to provide a bone tray for carrying bone implant material which tray will fit into the distractor.

It is yet another objective of this invention to provide a tool for insertion and manipulation of the distractor and the bone tray.

It is a still further objective of this invention to provide a retainer to attach the distractor and the bone tray together.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
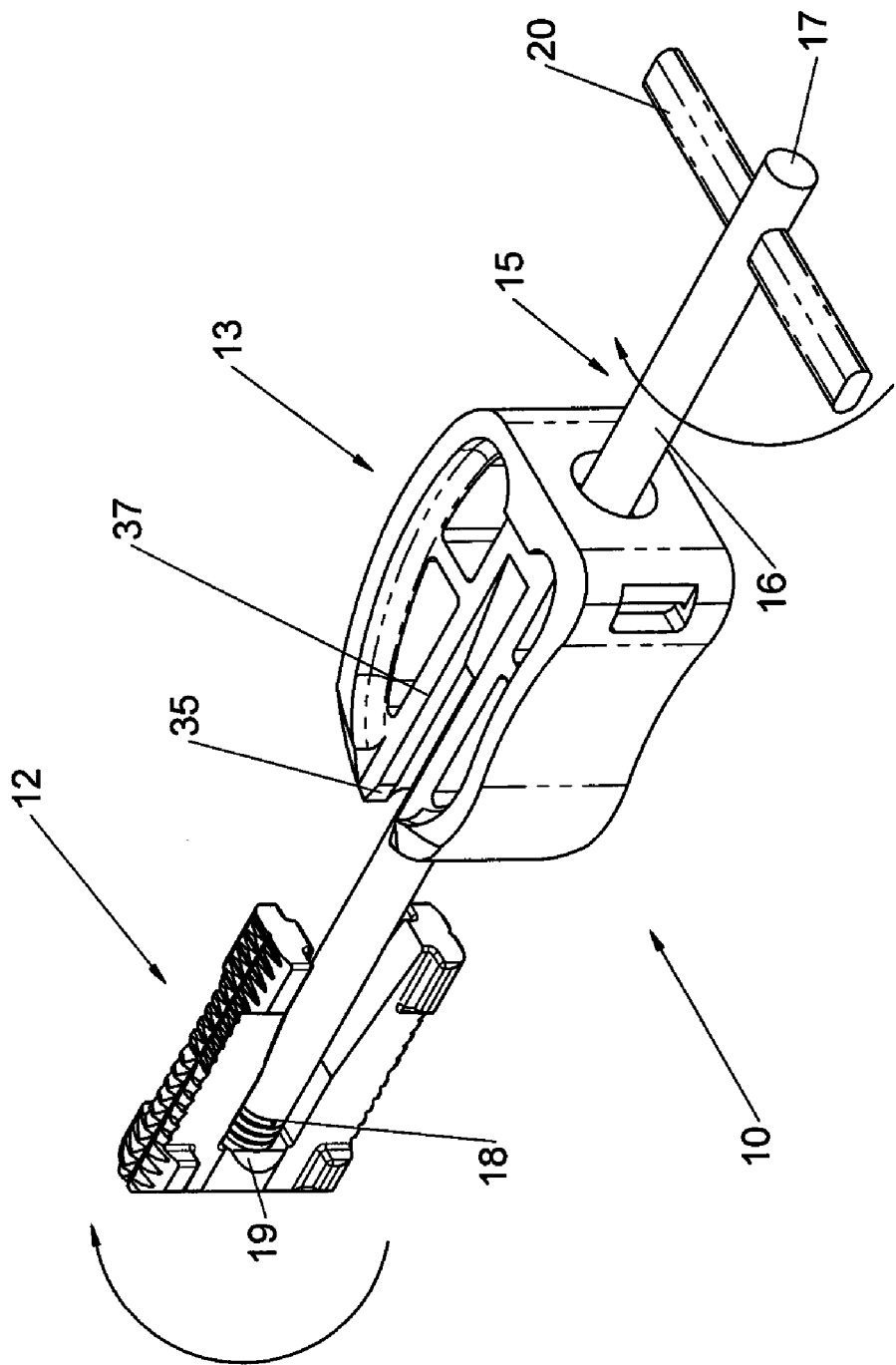
FIG. 1 is a perspective view of the spinal implant and insertion tool of this invention.

The spinal implant kit 10, as shown in FIG. 1, includes an insertion tool 15 which is made up of a sleeve 16 and a rod 17. The rod 17 is threaded into the aperture in the distractor 12 and the sleeve 16 is telescoped over the rod. The leading end 18 of the sleeve has a slot 19 that slides over the base of the distractor to apply torque to the distractor. The other end of the sleeve has a handle 20 by which the surgeon rotates the sleeve 16 thereby rotating the distractor 12. This allows the sleeve to be removed after the distractor is in place leaving the rod for use in guiding the bone tray 13 into the surgical site.

While the illustrated components are considered the preferred embodiment, there are other alternative structures acceptable. For example, the rod may have a bayonet or other reversible connection with the distractor. And the sleeve may be omitted with only a removable handle fitted on the rod, as by a slot or aperture, to apply torque to the distractor.

Figure 2:
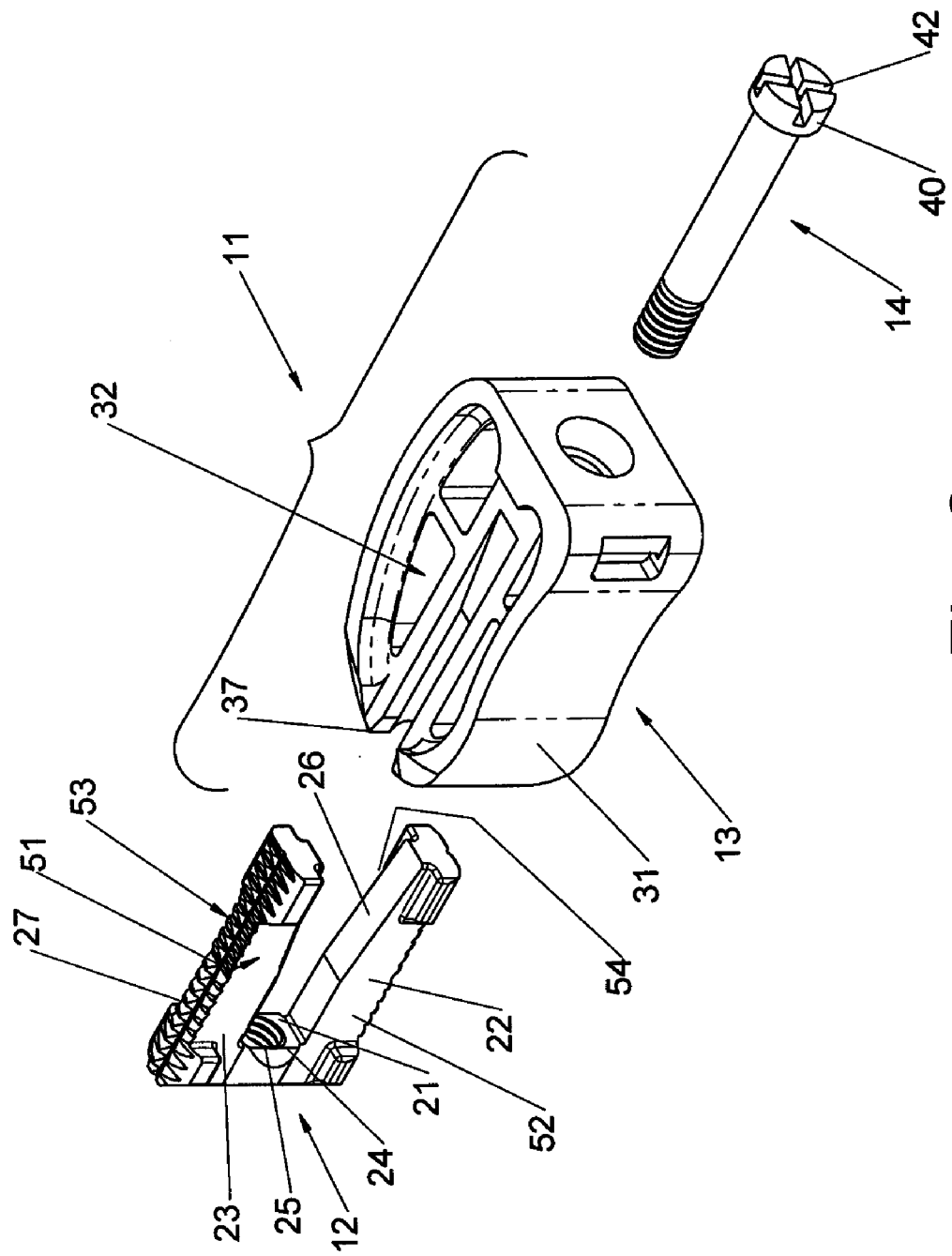
FIG. 2 is an exploded perspective view of the spinal implant of this invention.
Figure 4:
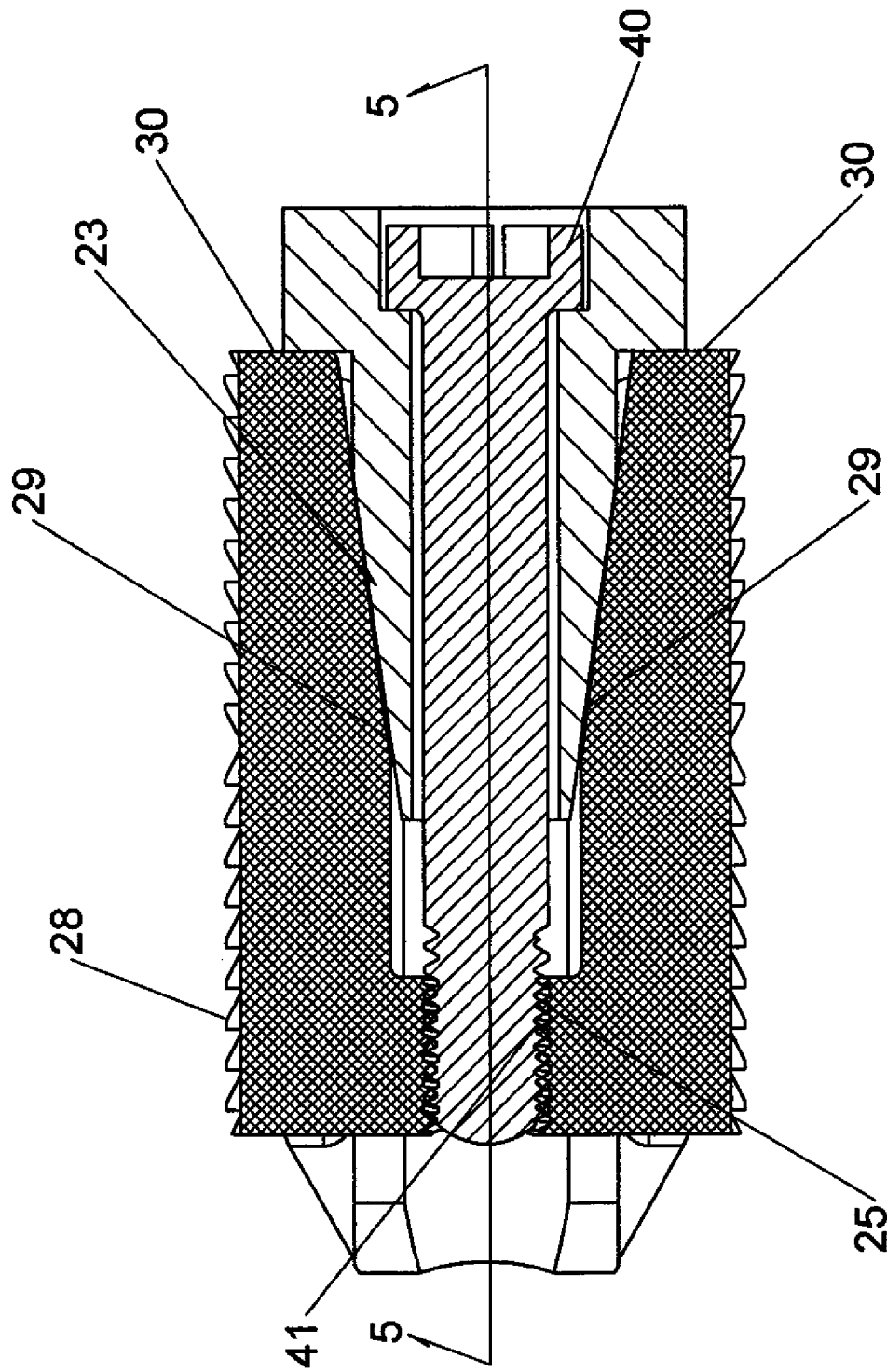
FIG. 4 is a cross section along line 4-4 of FIG. 3.

The spinal cage 11, as shown in FIG. 2, has a U-shaped distractor 12, an elliptical bone tray 13 and a retainer 14. The U-shaped distractor 12 has a base 21 connected at each end to a leg 22 and a leg 23. The base 21 has an aperture 24 shown with threads 25 in FIGS. 2, 4, and 5. Each leg has an interior surface 26 and an exterior surface 27 connected by planar side surfaces. The exterior surface of each leg has a series of serrations 28. The serrations may be normal to the exterior surface or slanted, as shown in FIG. 4, or pyramidal to provide purchase for the distractor in the end plates of the vertebrae to prevent shifting of position.

Figure 3:
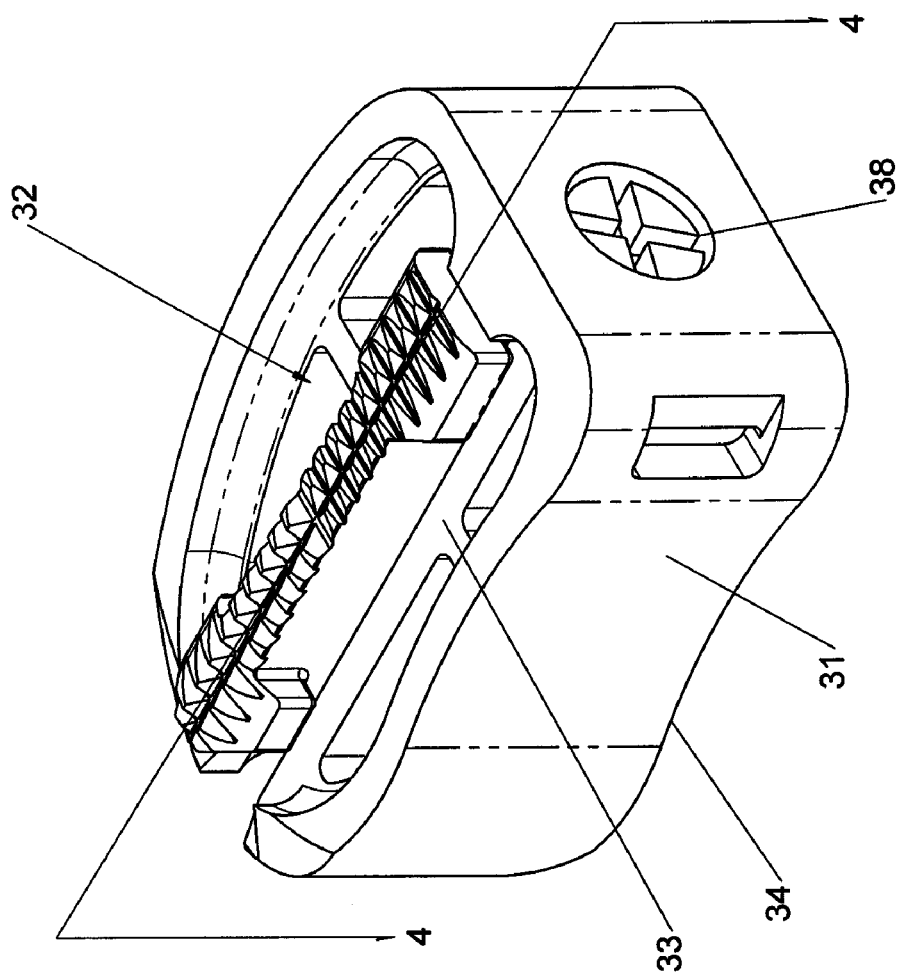
FIG. 3 is a perspective view of the assembled spinal implant of this invention.

The interior surface 26 of each leg is illustrated with a keel 29 that tapers from a thicker end near the base to a thinner free end 30. The keel 29 is of a size and shape to slide in the guide formed in the sidewall of the bone tray. The free end 30 acts as a stop by contacting the sidewall of the bone tray in the proper assembly of the components, see FIG. 3.

Figure 5:
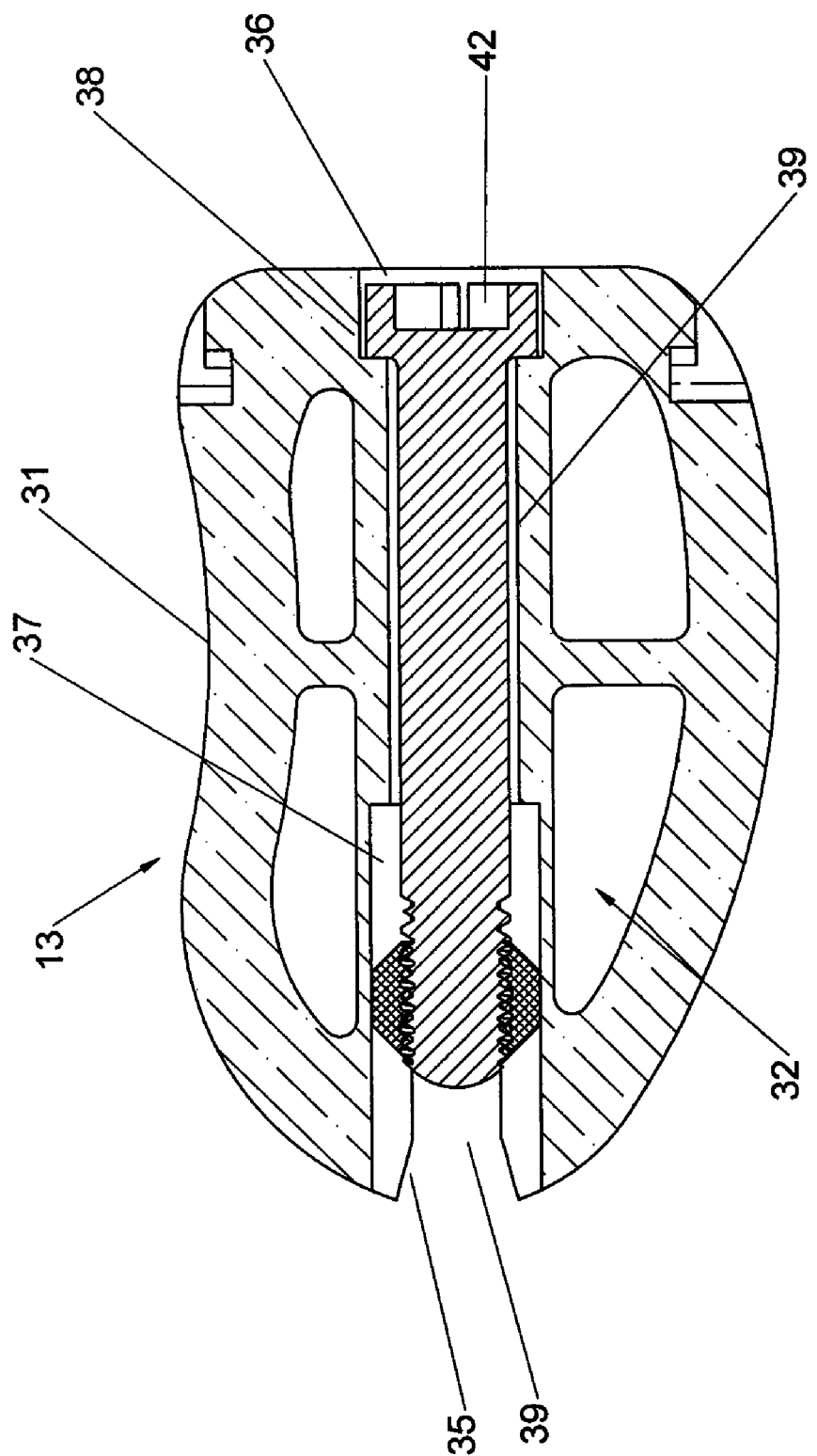
FIG. 5 is a cross section along line 5-5 of FIG. 4

The bone tray 13, shown in FIGS. 1, 2, and 5, has an elliptical outline or other shape formed by a continuous sidewall 31 which defines a hollow interior 32. The hollow interior 32 may be filled with bone growth or other material (not shown), as mentioned above. The bone tray 13 has an open top surface 33 and an open bottom surface 34 which contact the end plates of the adjacent vertebrae after implantation in the spine. The hollow interior provides a pathway for boney ingrowth between the adjacent vertebrae.

The continuous sidewall 31 doubles back on itself in an inversion portion 35. The inversion portion extends through the hollow interior and terminates in contact with the opposite side of the sidewall. At the contact point between the sidewall and the inversion portion, there is a bore 36 through the sidewall and the inversion portion. The inversion portion 35 results in an elongated opening 37 that extends from the top surface 33 to the bottom surface 34 and spans a major portion of the elliptical bone tray 13.

The bore 36 has a countersunk mouth 38 and a smaller shaft 39 which cooperate with the retainer 14. The countersunk mouth accepts the head of the retainer and acts as a bearing surface for the head. The shaft 39 guides the retainer through the opening 37 to engage the aperture 24 in the distractor 12.

The retainer 14, as shown in FIGS. 2, 4 and 5, is a bolt having an enlarged head 40 on the trailing end and threads 41 on the leading end. The threads 41 cooperate with the threads 25 in the aperture 14 to provide a rotational connection. The enlarged head 40 has a slot 42 for fitting a tool to provide torque to the bolt.

The simplified procedure made possible by this spinal implant 10 reduces the number of instruments necessary to prepare the implant site by permanently incorporating the distractor 12 into the cage 11. After the implant site has been exposed by a small surgical incision, the distractor 12 is introduced between the vertebrae with the flat sides 51 and 52 of the legs 22, 23 contacting the end plate of one vertebra and the flat sides 53, 54 of the legs 22, 23 contacting the end plate of the adjacent vertebra. The distractor is inserted using the rod 17 and sleeve 16. Once in the desired location, the sleeve is rotated 90 degrees rotating the distractor and placing the serrations 28 of each leg of the distractor in contact with a different end plate recreating the intervertebral space. The sleeve 16 and handle 20 are removed from the rod 17.

The distal end of the rod is placed in the bore of the bone tray and the tray in moved along the rod until the opening in the bone tray 13 engages the keel of the distractor 12. The bone tray is guided into proper alignment with the distractor and the free end 30 of the distractor is stopped by the sidewall 31 of the bone tray. The rod is then uncoupled from the aperture 21 in the distractor and removed.

The retainer 14 is then inserted into the bore 39 of the bone tray 13 and guided into rotational contact with the aperture in the distractor. Torque is applied to the retainer which draws the distractor and the bone tray into intimate contact completing the procedure.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

What is claimed is:

1. A spinal implant kit for fusing adjacent vertebrae comprising an elongated tool, a distractor, a bone tray, and a retainer, said distractor having a base and two legs, each leg joined at one end to said base forming a U-shaped outline, said base having a removable attachment removably connected to an end of said elongated tool, each leg having serrations adapted to engage the end plates of adjacent vertebrae, respectively, said bone tray having an open top side and an open bottom side, said top side and said bottom side adapted to engage the end plates of adjacent vertebrae, respectively, said bone tray having a sidewall connecting said top side and said bottom side, said sidewall having a bore therethrough, said tool slidably extending through said bore whereby said distractor is adapted to be inserted between adjacent vertebrae using said tool, said tool adapted to rotate said distractor to engage said serrations and the end plates, said bone tray is adapted to slide along said tool to contact said distractor, said tool is adapted to be removed from said removable attachment of said distractor and said bone tray, and said retainer is adapted to be inserted into said bore in said bone tray and said retainer is affixed to said removable attachment in said distractor locking said bone tray and said distractor together, and a sleeve removably telescoped over said tool, said sleeve extending through said bore in said bone tray and connected to said distractor, said sleeve including a handle for rotating said sleeve and said distractor whereby rotation of said sleeve 90 degrees rotates said distractor 90 degrees.

2. A spinal implant kit for fusing adjacent vertebrae of claim 1 comprising several distractors and several bone trays, each of said distractors and each of said bone trays being of different dimensions.

3. A spinal implant kit for fusing adjacent vertebrae of claim 1 comprising said sidewall at said top side of said bone tray having a guide adapted to slidably connect with one of said legs of said distractor to align said distractor and said bone tray.

4. A spinal implant kit for fusing adjacent vertebrae of claim 3 comprising said sidewall at said bottom side of said bone tray having a guide adapted to slidably connect with one of said legs of said distractor to align said distractor and said bone tray.

5. A spinal implant kit for fusing adjacent vertebrae of claim 1 comprising said sidewall at said bottom side of said bone tray having a guide adapted to slidably connect with one of said legs of said distractor to align said distractor and said bone tray.

* * * * *